(12) United States Patent
Yuan et al.

(10) Patent No.: US 11,445,711 B2
(45) Date of Patent: Sep. 20, 2022

(54) INTELLIGENT SEPARATION AND DRYING SYSTEM FOR MAGGOTS AND METHOD OF OPERATING SAME

(71) Applicant: Lishui Institute of Ecology and Environment,Nanjing University, Jiangsu (CN)

(72) Inventors: Zengwei Yuan, Jiangsu (CN); Shiwen Zhang, Jiangsu (CN); Zumao Qin, Jiangsu (CN); Xinrong Zhou, Jiangsu (CN); Tianming Chen, Jiangsu (CN)

(73) Assignee: Lishui Institute of Ecology and Environment, Nanjing University, Nanjing (CN)

( * ) Notice: Subject to any disclaimer, the term of this patent is extended or adjusted under 35 U.S.C. 154(b) by 109 days.

(21) Appl. No.: 16/925,263

(22) Filed: Jul. 9, 2020

(65) Prior Publication Data
US 2021/0144905 A1     May 20, 2021

Related U.S. Application Data

(63) Continuation of application No. PCT/CN2020/078728, filed on Mar. 11, 2020.

(30) Foreign Application Priority Data

Nov. 18, 2019    (CN) .......................... 201911127903.5

(51) Int. Cl.
*A01K 67/033*     (2006.01)
*C02F 3/32*     (2006.01)
*C02F 103/20*     (2006.01)

(52) U.S. Cl.
CPC ............ *A01K 67/033* (2013.01); *C02F 3/327* (2013.01); *C02F 2103/20* (2013.01)

(58) Field of Classification Search
CPC .............................. A01K 67/033; A01K 61/90
See application file for complete search history.

(56) References Cited

U.S. PATENT DOCUMENTS

2015/0223496 A1*   8/2015   Kitazumi ............. A01K 67/033
                                                                                           119/6.5

FOREIGN PATENT DOCUMENTS

| CN | 102026555 | A | * | 4/2011 | ............... A23K 1/10 |
| CN | 104161018 | A | | 11/2014 | |
| CN | 107125211 | A | * | 9/2017 | ........... A01K 67/033 |
| CN | 207252610 | U | | 4/2018 | |
| WO | WO-2016015639 | A1 | * | 2/2016 | ........... A01K 67/033 |

* cited by examiner

*Primary Examiner* — Magdalena Topolski
*Assistant Examiner* — Alanna K Peterson (57) ABSTRACT

Disclosed are an intelligent separation and drying system for maggots and a method of operating the same. The intelligent separation and drying system includes an intelligent light control unit, an intelligent scraping unit, a separation unit, a drying unit, a travelling unit and a central control unit. The central control unit is connected to other units through signals. Multidisciplinary techniques, including spectrum analysis, machine learning algorithm and artificial neural network, are combined to automatically, systematically, intelligently and continuously separate maggots and maggot feed as well as dry the maggots with high efficiency in a clean manner.

8 Claims, 4 Drawing Sheets

INTELLIGENT SEPARATION AND DRYING SYSTEM FOR MAGGOTS AND METHOD OF OPERATING SAME

CROSS-REFERENCE TO RELATED APPLICATIONS

This application is a continuation of International Patent Application No. PCT/CN2020/078728, filed on Mar. 11, 2020, which claims the benefit of priority from Chinese Patent Application No. 201911127903.5, filed on Nov. 18, 2019. The content of the aforementioned applications, including any intervening amendments thereto, is incorporated herein by reference.

TECHNICAL FIELD

The present application relates to maggot breeding and automatic separation equipment, and more particularly to an intelligent separation and drying system for maggots and a method of operating the same.

BACKGROUND

Maggot separation plays a critical role in the process of breeding maggots to treat the excrement from livestock and poultry to produce proteins. Inappropriate separation will not only cause waste in manpower, material resources and maggot proteins, but also cause environmental pollution since the maggots will undergo nymphosis to turn into flies, departing from the original intention of green farming. Currently, the separation of the maggots and maggot feed is implemented mainly through artificially vibrating a sieve to allow the maggots to fall from the sieve to be collected, which leads to a low separation efficiency. For the purpose of improving separation efficiency, some automatic devices are developed and described as follows.

Chinese Patent Application No. 201720517377.3 discloses a maggot separator, including a rack as well as a raw material feeding mechanism, a maggot separation mechanism, a maggot collection mechanism and a travelling mechanism, which are provided on the rack. The maggot separation mechanism includes a stacking box, a lifting holder and a lifting mechanism that drives the lifting holder to move up and down. An opening is provided at a side of the stacking box, and a baffle plate is provided at the outside the stacking box at the opening. The baffle plate is fixedly connected to the lifting holder to move up and down along with the lifting holder. The lifting holder is provided with a scraper which can move up and down along with the lifting holder. A scraper driving mechanism is provided between the scraper and the lifting holder to drive the scraper to move back and forth in the direction of the opening. A lower edge of the scraper is not lower than an upper edge of the baffle plate. The maggot separator provided herein employs a separation plate and a maggot blocking plate to separate maggots and waste, allowing for higher purity in the separated maggots.

Chinese Patent Application No. 201410399299.2 discloses another maggot separator, including a body and a feeding device provided at a front end thereof. The feeding device is connected to a front end of a groove-shaped feed container fixed on the body for conveying maggots and material residues. A vertical lifting device is provided on the groove-shaped feed container. A top of the vertical lifting device is provided with a cleaning device that moves backwards and forwards in a direction perpendicular to a travelling direction of the body. A gate is suspended respectively from two ends of the vertical lifting device through a connecting rod. The gate is close to an end face of a notch at each of two ends of the groove-shaped feed container. A collection device is fixed on the body and provided under the end face. The maggot separator provided herein uses automatic equipment and the propensity of maggots that they are prone to moving downward to separate maggots, which greatly reduces the labor intensity and improves the efficiency of separating maggots from the material residues.

However, in the above-mentioned disclosures, the separation efficiency and breeding environment are not satisfactory enough, so it is still required to improve the existing equipment with regard to these two aspects.

SUMMARY

In order to solve the problems in the prior art that the separation efficiency and breeding environment are not satisfactory enough, this application provides an intelligent separation and drying system for maggots and a method of operating the same.

The technical solutions of the application are described as follows.

In a first aspect, the application provides an intelligent separation and drying system for maggots, comprising: an intelligent light control unit, an intelligent scraping unit, a separation unit, a drying unit, a travelling unit and a central control unit.

The intelligent light control unit comprises a sunlight transmission module, an additional light and an infrared sensor to realize a function of automatically controlling light.

The intelligent scraping unit comprises a multi-layered scraper assembly, a residue collecting tray and a first weight sensor to realize a function of rapidly scraping maggot residues.

The separation unit comprises a breeding tray, a multi-layered sieve, a maggot receiving and drying tray and the residue collecting tray to realize automatic separation.

The intelligent scraping unit and the separation unit share the residue collecting tray.

The drying unit comprises a solar accumulator, a heat collector, a moisture sensor, a temperature sensor, a second weight sensor, the maggot receiving and drying tray and a blower to realize the rapid drying.

The drying unit and the separation unit share the maggot receiving and drying tray.

The travelling unit comprises a horizontal driving wheel, a vertical lifting platform and an infrared detector to automatically adjust heights of the breeding tray, the multi-layered sieve and the maggot receiving and drying tray as well as automatically transfer the breeding tray, the multi-layered sieve and the maggot receiving and drying tray.

The central control unit comprises an intelligent control module, a data management module and an odor alarm module; the intelligent control module is connected to the intelligent light control unit, the intelligent scraping unit, the separation unit, the drying unit and the travelling unit, respectively, to realize the functions of automatically monitoring, intelligently managing and adjusting the system and devices; the odor alarm module acquires data through an odor sensor provided at a data acquisition end and issues an alert. The data acquired by the odor sensor is processed by the data management module and then sent to the odor alarm module. When the collected odor exceeds a preset odor value of the odor alarm module, the odor alarm module begins to issue an alert.

The application employs the combination of multidisciplinary techniques, such as spectrum analysis, machine learning algorithm and artificial neural network, and a plurality of sensors to realize intelligent learning and provide a fully-automatic, systematic and intelligent method to continuously separate maggots from maggot feed and dry the maggots with high efficiency in a clean manner. The system also has the functions of self-monitoring, self-regulation and self-management, which are conducive to the large-scale intelligent breeding of maggots. Moreover, the application makes full use of the growth characteristics of maggots that they are photophobic and naturally crawl into holes to realize the intelligent and batchwise separation of maggots and maggot feed, which not only improves the separation efficiency, but also improves the quality and purity of dried maggots and maggot feed.

In some embodiments, the sunlight transmission module comprises a light-capturing zone, a light transmission zone and an irradiation zone.

In some embodiments, the light-capturing zone is provided with a light-capturing cover and a solar panel; the light transmission zone employs an anti-corrosion and anti-rust material and a reflective film is attached to an interior of the light transmission zone to transmit sunlight; and the infrared sensor and the additional light are provided in the irradiation zone; a photometer is also provided in the irradiation zone to measure sunlight intensity, and the additional light is switched on when the measured sunlight intensity is below 500 Lux.

In some embodiments, the multi-layered scraper assembly comprises a rotating shaft, sprockets, a chain and scrapers; the sprockets are respectively provided at two ends and a middle of the rotating shaft; and the chain for driving the sprockets at the two ends of the rotating shaft is provided with the scrapers.

In some embodiments, at least three scrapers are provided; the scrapers are arc-shaped and have different lengths to obtain a scraping depth range of 4-15 mm; and scraping by layers of the scrapers and irradiation by the intelligent light control unit are alternately performed, wherein each layer of the scrapers works after the intelligent light control unit has worked for 1-3 min.

The scraping time is set according to the growth characteristics of maggots. Based on the nature that the maggots are prone to crawling into the gaps, it can be deduced that when there are 20 maggots per square meter, almost all the maggots have arrived at a lower part within 1-3 min and only the residues are left. Therefore, scraping by layers of the scrapers and irradiation by the intelligent light control unit are alternately performed, and the scrapers are set to start to work after the intelligent light control unit has worked for 1-3 min to ensure that most of the maggots have already moved to a lower part, thereby minimizing the number of maggots that are scraped away along with residues.

In some embodiments, the drying unit utilizes solar energy to dry the maggots. The maggot receiving and drying tray is provided with an upper partition plate and a lower partition plate, which are both composed of a grid with a mesh size of $0.5$ $cm^2$ and a withdrawable plate, and the withdrawable plate can be pulled out during the drying.

The upper partition plate and the lower partition plate are provided based on the growth characteristics of maggots that they are prone to crawling into the crevices. After the maggots move to the lower partition plate, the maggot residues are left on the upper partition plate to realize an automatic separation of the maggots and the maggot residues. During the drying, the upper partition plate is pulled out to allow half of the maggots to drop down to the lower partition plate to decrease the density of the maggots, thereby improving the drying efficiency.

In some embodiments, the data management module comprises a data acquisition module and a data analysis module to perform self-learning and self-updating of database; the data acquisition module is connected to the infrared sensor, the first weight sensor, the second weight sensor, the infrared detector, the temperature sensor, the moisture sensor and the odor sensor which are provided at the data acquisition end; and the data analysis module is used to analyze a moisture content of the maggot feed, maggot biomass and pre-estimate daily maggot biomass and daily amount of maggot excrement.

In some embodiments, the separation unit uploads detected maggot sizes to the central control unit; the central control unit adjusts the multi-layered sieve of the separation unit to a mesh size of 0.8-1.5 $cm^2$; a distance between the multi-layered sieve and the maggot receiving and drying tray is equal to or less than 2 cm.

The mesh size of the multi-layered sieve is adjusted to 0.8 $cm^2$ to 1.5 $cm^2$ according to the size of the mature maggots to enable the maggots to pass through the sieve holes and fall onto the maggot receiving and drying tray, and thus they are separated based on the characteristic of the maggots that they are prone to crawling into the holes. The distance between the multi-layered sieve and the maggot receiving and drying tray is set to be equal to or less than 2 cm also based on such characteristic. A large distance between the multi-layered sieve and the maggot receiving and drying tray will negatively affect the efficiency of passing through the sieve holes, affecting the separation efficiency.

In some embodiments, the infrared sensor in the irradiation zone performs real-time detection of biomass of maggots on the breeding tray within a scraping depth that a lower layer of the scrapers in the intelligent scraping unit reach, when there are more than 20 maggots per square meter, the central control unit adjusts illuminating intensity and illuminating time of the intelligent light control unit and also adjusts a depth that the scrapers in the intelligent scraping unit reach.

The illuminating intensity and the illuminating time are adjusted to check the biological activity of the maggots. The failure to pass through the sieve holes within 3 min under irradiation indicates that these maggots have low activity and hardly survive, based on which the growth status of the maggots can be determined.

In some embodiments, the multi-layered scraper assembly is provided with the first weight sensor, so that a comparison is made between a weight of residues scraped by each layer of the scrapers and a weight of residues having a moisture content of 60% stored in the central control unit to start or stop scraping; when the scraped residues have a moisture content of more than 60%, the lower one of the layers of the scrapers stops scraping, and simultaneously the breeding tray is returned to a breeding area for standing.

The operation of the scrapers is controlled by comparing the weight of the scraped residues with the weight of residues having a moisture content of 60%. When the weight of the scraped residues exceeds the weight of the residues having the moisture content of 60%, it indicates that the scraped residues contain a considerable number of maggots, at this time, it also indicates that the maggots have poor growth and fail to pass through the sieve holes within 1-3 min under irradiation.

In a second aspect, the application provides a method of operating the intelligent separation and drying system for the maggots, comprising:

1) switching on the intelligent separation and drying system to breed maggots; detecting the biomass of maggots in the breeding tray in real time through the infrared sensor in the irradiation zone of the intelligent light control unit; wherein when there are more than 20 maggots per square meter, the intelligent light control unit is switched on to perform irradiation via the sunlight transmission module; when the sunlight intensity measured by the photometer is below 500 Lux, the additional light is switched on to drive the maggots to crawl down to the multi-layered sieve;

2) when less than 20 maggots per square meter in the breeding tray are detected by the infrared sensor of the intelligent light control unit in real time, operating the multi-layered scraper assembly to scrape maggot feed to the residue collecting tray, wherein a scraping depth range of the multi-layered scraper assembly is self-adjusted within 4-15 mm according to the maggot biomass; after each layer of the scrapers performs scraping, continuously illuminating the breeding tray for 1-3 min, wherein when each layer of the scrapers works, the first weight sensor provided on the multi-layered scraper assembly uploads a weight of scraped residue to the data analysis module to make a comparison between the weight of the scraped residue and a weight of residues having a moisture content of 60% stored in the central control unit; if the scraped residues have a moisture content of more than 60%, the scrapers stop scraping residues, and the breeding tray is returned to a breeding area for standing through the vertical lifting platform and the horizontal driving wheel of the travelling unit; and when more than 20 maggots per square meter in the breeding tray are detected by the infrared sensor of the intelligent light control unit in real time, adjusting illuminating intensity, illuminating time and the scraping depth of the scrapers through the central control unit to ensure a complete scraping of residue;

3) after the residues are scraped, detecting a size of the maggots crawling down to the multi-layered sieve through the infrared sensor of the intelligent light control unit and uploading the size of the maggots to the central control unit to timely adjust a mesh size of the multi-layered sieve of the separation unit to be 0.8-1.5 $cm^2$, wherein a distance between the multi-layered sieve and the maggot receiving and drying tray is equal to or less than 2 cm; and 4) when a height of maggot residues is detected through an overflow device provided on the residue collecting tray to exceed ⅘ of a height of the residue collecting tray, stopping collecting residues to the residue collecting tray; uploading a weight of fresh maggots to the data management module through the second weight sensor provided on the maggot receiving and drying tray; and transferring the maggot receiving and drying tray to the drying unit through the vertical lifting platform and the horizontal driving wheel of the travelling unit; and after the maggot receiving and drying tray arrives at the drying unit, pulling out the upper partition plate of the maggot receiving and drying tray to allow half of the fresh maggots on the upper partition plate to drop down to the lower partition plate of the maggot receiving and drying tray; switching on the heat collector and the blower of the drying unit to dry the maggots on the maggot receiving and drying tray while monitoring a drying temperature by the infrared detector, wherein after the drying is completed, dried maggots on the upper partition plate are blown to drop down to the lower partition plate; uploading a weight of the dried maggots to the data management unit through the second weight sensor; and pulling out the lower partition plate to collect the dried maggots in a bag.

Compared to the prior art, this application has the following benefits.

1) The application employs multidisciplinary techniques such as spectrum analysis, machine learning algorithm and artificial neural network to provide a fully automatic, systematic and intelligent system to continuously separate maggots and feed and dry the maggots with high efficiency in a clean manner, thereby reducing labor consumption. The system also has the functions of self-monitoring, self-regulation and self-management, which are conducive to the large-scale intelligent breeding of maggots.

2) Based on the combination of growth characteristics of maggots, spectrum analysis and machine learning algorithm, the application realizes the intelligent and batchwise separation of maggots and maggot feed, which can not only improve the separation efficiency, but also improve the quality and purity of dried maggots and maggot feed.

3) The application fully utilizes solar energy for illumination and drying, so that the pollution and energy consumption are minimized in the whole process, facilitating the combination of environmental improvement, resource recovery and clean energy utilization and expanding the application range.

In the drawings: 1, light-capturing cover; 2, solar panel; 3, light transmission zone; 4, heat collector; 5, blower; 7, breeding tray; 9, residue collecting tray; 10, vertical lifting platform; 11, maggot receiving and drying tray; 14, reflective film; 15, additional light; 16, scraper; 17, sprocket; 18, chain; 19, multi-layered sieve; 26, upper partition plate; 27, lower partition plate; and 28, horizontal driving wheel.

DETAILED DESCRIPTION OF EMBODIMENTS

The application will be further described below with reference to the accompany drawing.

An intelligent separation and drying system for maggots includes an intelligent light control unit, an intelligent scraping unit, a separation unit, a drying unit, a travelling unit and a central control unit. A structural frame of the intelligent separation and drying system for the maggots is shown in the FIGS. 1-3.

Figure 1:
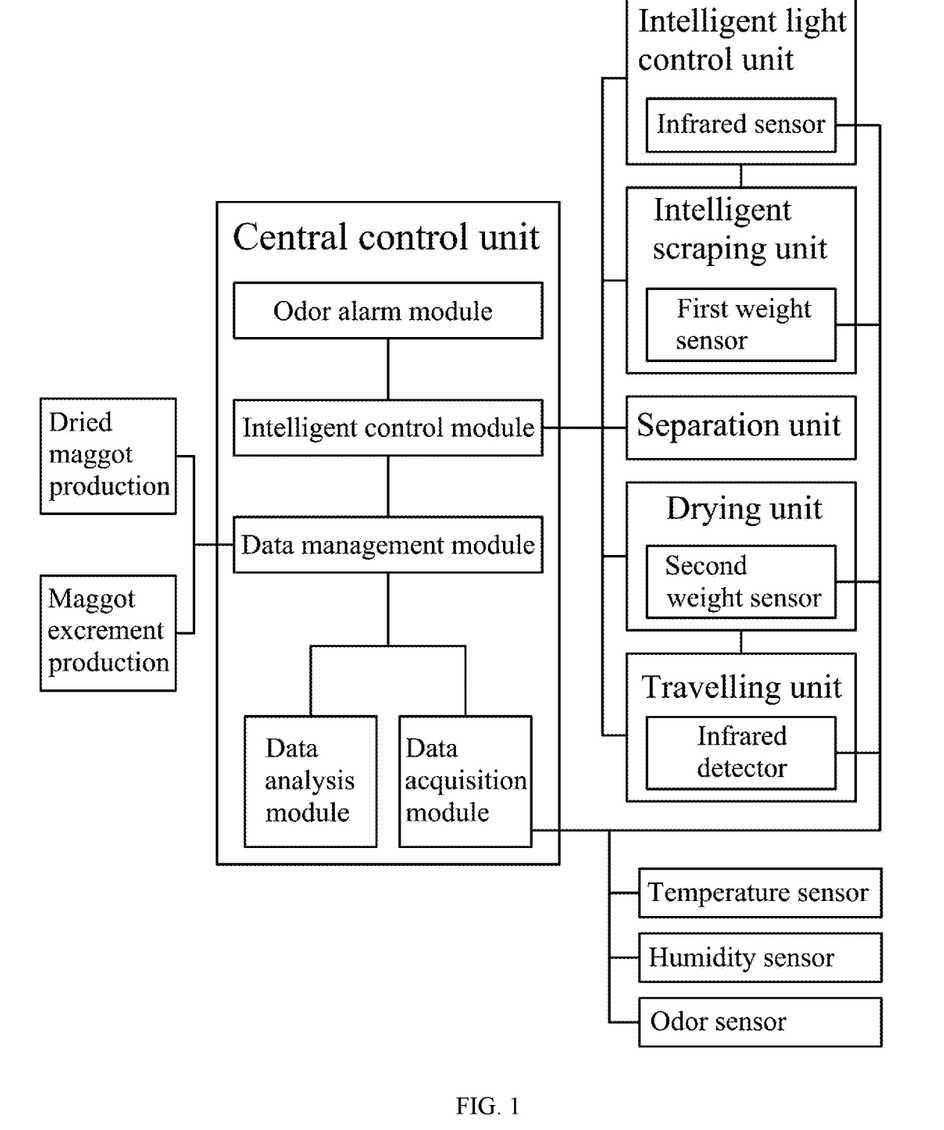
FIG. 1 schematically shows a structural frame of an intelligent separation and drying system for maggots according to the present application.
Figure 2:
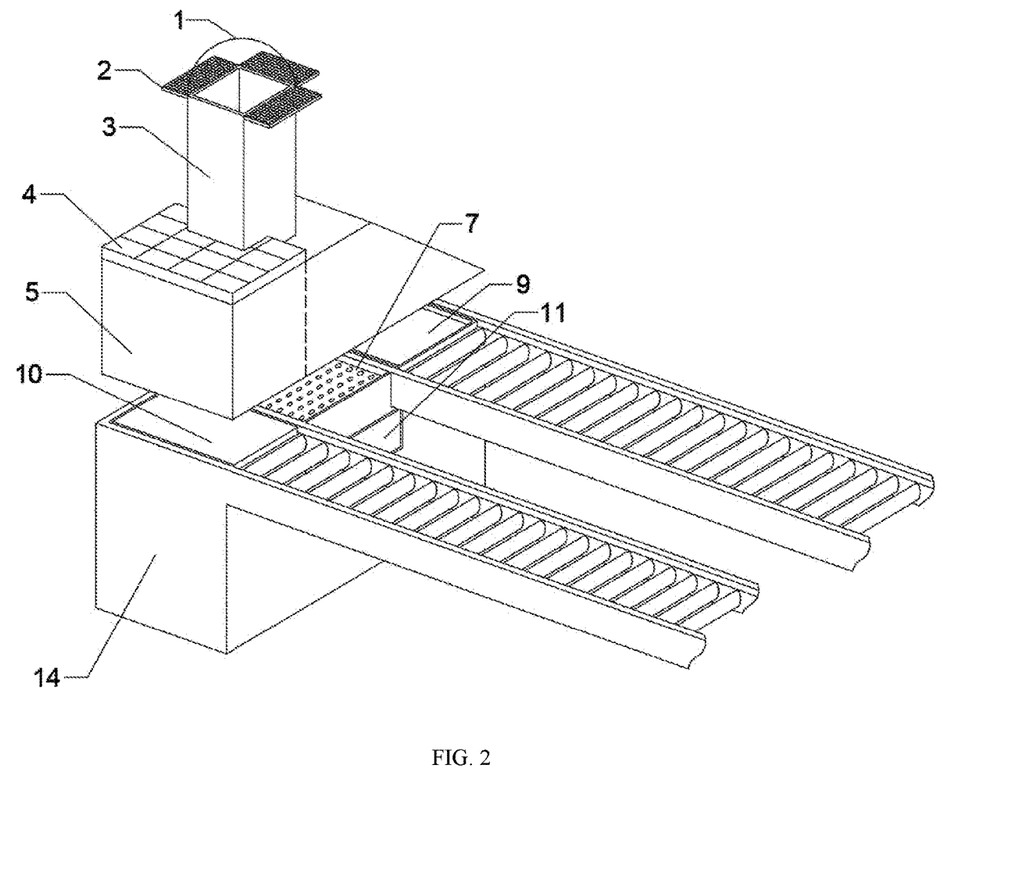
FIG. 2 schematically shows the intelligent separation and drying device for maggots according to an embodiment of the present disclosure.
Figure 3:
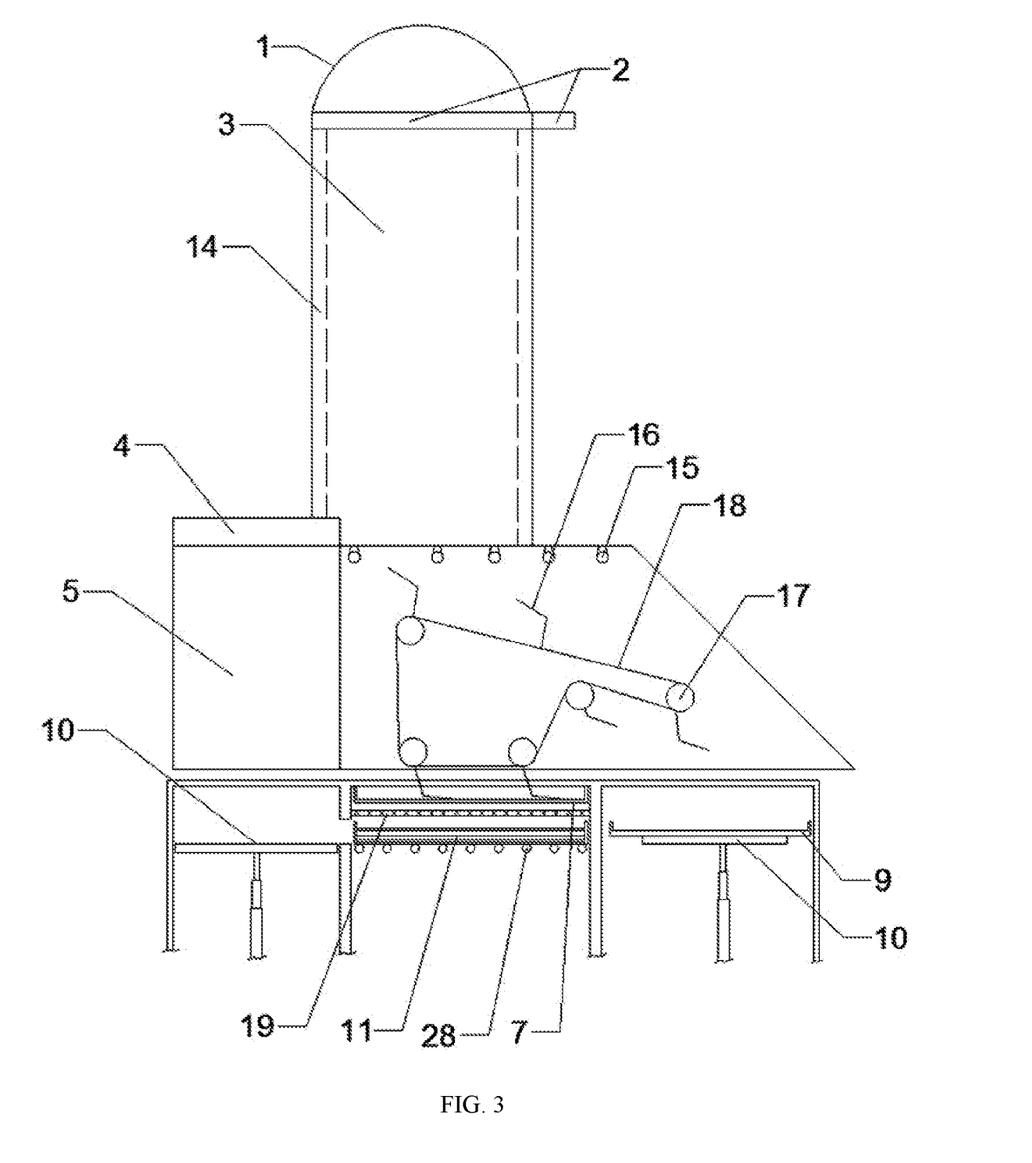
FIG. 3 is a cross-sectional view of the intelligent separation and drying device for maggots according to an embodiment of the present disclosure.

The intelligent light control unit includes a sunlight transmission module, an additional light 15 and an infrared sensor to automatically control the light; the sunlight transmission module includes a light-capturing zone, a light transmission zone 3 and an irradiation zone; the light-capturing zone is provided with a light-capturing cover 1 and a solar panel 2; the light transmission zone employs an anti-corrosion and anti-rust material; and a reflective film 14 is attached to an interior of the light transmission zone to transmit sunlight; the infrared sensor and the additional light are provided in the irradiation zone; a photometer is also provided in the irradiation zone to measure sunlight intensity, and the additional light is switched on when the measured sunlight intensity is below 500 Lux; the infrared sensor in the irradiation zone performs real-time detection of biomass of maggots on the breeding tray within a scraping depth that a lower layer of the scrapers in the intelligent scraping unit reach; when there are more than 20 maggots per square meter, the central control unit adjusts illuminating intensity and illuminating time of the intelligent light control unit and also adjusts a depth that the scrapers in the intelligent scraping unit reach.

The intelligent scraping unit includes a multi-layered scraper assembly, a residue collecting tray 9 and a first weight sensor to rapidly scrape maggot residues; the multi-layered scraper assembly includes a rotating shaft, sprockets 17, a chain 18 and scrapers 16; the sprockets are respectively provided at two ends and a middle of the rotating shaft; and the chain for driving the sprockets at the two ends of the rotating shaft is provided with the scrapers 16; at least three scrapers are provided; the scrapers are arc-shaped and have different lengths to obtain a scraping depth range of 4-15 mm; scraping by layers of the scrapers and irradiation by the intelligent light control unit are alternately performed, and each layer of the scrapers works after the intelligent light control unit has worked for 1-3 min.

The multi-layered scraper assembly is provided with the first weight sensor to make a comparison between a weight of residues scraped by each layer of scrapers and a weight of residues having a moisture content of 60% stored in the central control unit to start or stop scraping; when the scraped residues have a moisture content of more than 60%, the lower layer of the scrapers stops scraping, and simultaneously the breeding tray is returned to a breeding area for standing.

The separation unit includes a breeding tray 7, a multi-layered sieve 19, a maggot receiving and drying tray 11 and the residue collecting tray 9 to realize an automatic separation function; the intelligent scraping unit and the separation unit share the residue collecting tray; the separation unit uploads detected maggot sizes to the central control unit; the central control unit adjusts the multi-layered sieve of the separation unit to a mesh size of 0.8-1.5 cm$^2$; a distance between the multi-layered sieve and the maggot receiving and drying tray is equal to or less than 2 cm.

Figure 4:
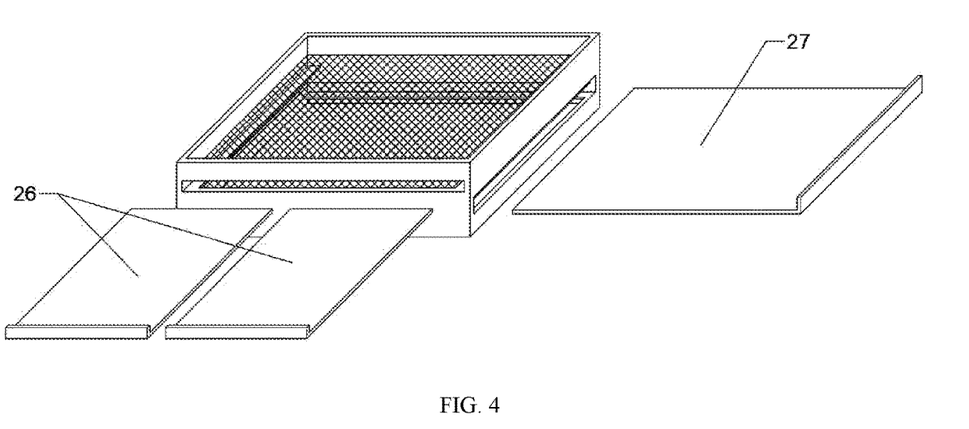
FIG. 4 schematically shows a maggot receiving and drying tray of the intelligent separation and drying device for maggots according to an embodiment of the present disclosure.

The drying unit includes a solar accumulator, a heat collector 4, a moisture sensor, a temperature sensor, a second weight sensor, the maggot receiving and drying tray 11 and a blower 5 to rapidly dry the maggots; the drying unit and the separation unit share the maggot receiving and drying tray; the drying unit preferentially utilizes solar energy to dry the maggots; as shown in FIG. 4, the maggot receiving and drying tray is provided with an upper partition plate 26 and a lower partition plate 27, which are both composed of a grid with a mesh size of 0.5 cm$^2$ and a withdrawable plate, and the withdrawable plate can be pulled out to be placed at a side during the drying to improve the drying efficiency of the maggots.

The travelling unit includes a horizontal driving wheel 28, a vertical lifting platform 10 and an infrared detector to allow a height and a position of the travelling unit to be automatically adjusted and shifted.

The central control unit includes an intelligent control module, a data management module and an odor alarm module to realize the functions of automatically monitoring, intelligently managing and adjusting the system and devices; the data management module includes a data acquisition module and a data analysis module to perform self-learning and self-updating of database; the data acquisition module is connected to the infrared sensor, the first weight sensor, the second weight sensor, the infrared detector, the temperature sensor, the moisture sensor and the odor sensor which are provided at the data acquisition end; the data analysis module is used to analyze a moisture content of the maggot feed, maggot biomass and pre-estimate daily maggot biomass and daily amount of maggot excrement; the odor alarm module acquires data through an odor sensor provided at the data acquisition end and issues an alert. The data acquired by the odor sensor is processed by the data management module and then sent to the odor alarm module. When the collected odor exceeds a preset odor value of the odor alarm module, the odor alarm module begins to issue an alert.

The embodiment provides a method of operating the intelligent separation and drying system for the maggots, which includes the following steps.

1) The intelligent separation and drying system is switched on to breed maggots. The biomass of maggots in the breeding tray is detected by the infrared sensor in the irradiation zone of the intelligent light control unit in real time. When there are more than 20 maggots per square meter, the intelligent light control unit is switched on to perform irradiation via the sunlight transmission module. When the sunlight intensity measured by the photometer is below 500 Lux, the additional light is switched on to drive the maggots to crawl down to the multi-layered sieve.

2) When less than 20 maggots per square meter in the breeding tray are detected by the infrared sensor of the intelligent light control unit in real time, the multi-layered scraper assembly starts to scrape maggot feed to the residue collecting tray, and a scraping depth range of the multi-layered scraper assembly is self-adjusted within 4-15 mm according to the maggot biomass. After each layer of the scrapers performs scraping, the breeding tray is illuminated for 1-3 min. When each layer of the scrapers works, the first weight sensor provided on the multi-layered scraper assembly uploads a weight of scraped residue to the data analysis module to make a comparison between the weight of the scraped residues and the weight of the residues having a moisture content of 60% stored in the central control unit, if the scraped residues have a moisture content of more than 60%, the scrapers stop scraping residues, and the breeding tray is returned to the breeding area for standing through the vertical lifting platform and the horizontal driving wheel of the travelling unit. When more than 20 maggots per square meter in the breeding tray are detected by the infrared sensor of the intelligent light control unit in real time, the illuminating intensity, illuminating time and the scraping depth of the scrapers are adjusted through the central control unit to ensure a complete scraping of residues.

3) After the residues are scraped, a size of the maggots crawling down to the multi-layered sieve is detected through the infrared sensor of the intelligent light control unit and the size of the maggots is uploaded to the central control unit to timely adjust a mesh size of the multi-layered sieve of the separation unit to 0.8-1.5 cm$^2$, and a distance between the multi-layered sieve and the maggot receiving and drying tray is equal to or less than 2 cm.

4) When a height of maggot residues is detected through an overflow device provided on the residue collecting tray to exceed ⅘ of a height of the residue collecting tray, the residue collecting tray stops collecting the residues; a weight of fresh maggots is uploaded to the data management module through the second weight sensor provided on the maggot receiving and drying tray. The maggot receiving and drying tray is then transferred to the drying unit through the vertical lifting platform and the horizontal driving wheel of the travelling unit.

After the maggot receiving and drying tray arrives at the drying unit, the upper partition plate of the maggot receiving and drying tray is pulled out to allow half of the fresh maggots on the upper partition plate to drop down to the lower partition plate of the maggot receiving and drying tray. Subsequently, the heat collector and the blower of the drying unit are switched on to rapidly dry the maggots on the maggot receiving and drying tray, while a drying temperature is monitored by the infrared detector. After the drying is completed, dried maggots on the upper partition plate are blown to drop down to the lower partition plate, and a weight of the dried maggots is uploaded to the data management unit through the second weight sensor. The lower partition plate is pulled out to collect the dried maggots in a bag.

It should be noted that the above embodiments are illustrative of the application and intended to further explain the present application. Unless otherwise specified, all technical and scientific terms used herein have the same meaning as commonly understood by those skilled in the art. It should be understood that these terms are merely illustrative and are not intended to limit the invention. As used herein, unless otherwise specified, the singular form may also include a plural form. In addition, it should be understood that the terms "comprise" and/or "include" in the description of the application indicate that features, steps, operation, devices, components and/or a combination thereof are included.

What is claimed is:

1. An intelligent separation and drying system for maggots, comprising:
    an intelligent light control unit,
    an intelligent scraping unit,
    a separation unit,
    a drying unit,
    a travelling unit, and
    a central control unit;
    wherein the intelligent light control unit comprises a sunlight transmission module, an additional light and an infrared sensor;
    the intelligent scraping unit comprises a multi-layered scraper assembly, a residue collecting tray and a first weight sensor;
    the separation unit comprises a breeding tray, a multi-layered sieve, a maggot receiving and drying tray and the residue collecting tray;
    the drying unit comprises a solar accumulator, a heat collector, a moisture sensor, a temperature sensor, a second weight sensor, the maggot receiving and drying tray and a blower;
    the travelling unit comprises a horizontal driving wheel, a vertical lifting platform and an infrared detector; and
    the central control unit comprises an intelligent control module, a data management module and an odor alarm module; the intelligent control module is connected to the intelligent light control unit, the intelligent scraping unit, the separation unit, the drying unit and the travelling unit, respectively; and the odor alarm module acquires data through an odor sensor provided at a data acquisition end and issues an alert.

2. The separation and drying system of claim 1, wherein the sunlight transmission module comprises a light-capturing zone, a light transmission zone and an irradiation zone;
    the light-capturing zone is provided with a light-capturing cover and a solar panel;
    the light transmission zone employs an anti-corrosion and anti-rust material; and a reflective film is attached to an interior of the light transmission zone to transmit sunlight; and
    the infrared sensor and the additional light are provided in the irradiation zone; a photometer is provided in the irradiation zone to measure sunlight intensity, and the additional light is switched on when the measured sunlight intensity is below 500 Lux.

3. The separation and drying system of claim 1, wherein the multi-layered scraper assembly comprises a rotating shaft, sprockets, a chain and scrapers; the sprockets are respectively provided at two ends and a middle of the rotating shaft; and the chain for driving the sprockets at the two ends of the rotating shaft is provided with the scrapers;
    at least three scrapers are provided; the scrapers are arc-shaped and have different lengths to obtain a scraping depth range of 4-15 mm; and scraping by layers of the scrapers and irradiation by the intelligent light control unit are alternately performed, wherein each layer of the scrapers works after the intelligent light control unit has worked for 1-3 min.

4. The separation and drying system of claim 1, wherein the drying unit dries the maggots through solar energy; the maggot receiving and drying tray is provided with an upper partition plate and a lower partition plate, which are both composed of a grid with a mesh size of 0.5 $cm^2$ and a withdrawable plate.

5. The separation and drying system of claim 1, wherein the data management module comprises a data acquisition module and a data analysis module to perform self-learning and self-updating of database;
    the data acquisition module is connected to the infrared sensor, the first weight sensor, the second weight sensor, the infrared detector, the temperature sensor, the moisture sensor and the odor sensor which are provided at the data acquisition end; and
    the data analysis module is used to analyze a moisture content of maggot feed, maggot biomass and pre-estimate daily maggot biomass and daily amount of maggot excrement.

6. The separation and drying system of claim 1, wherein the separation unit uploads detected maggot sizes to the central control unit; the central control unit adjusts the multi-layered sieve of the separation unit to a mesh size of 0.8-1.5 $cm^2$; a distance between the multi-layered sieve and the maggot receiving and drying tray is equal to or less than 2 cm.

7. The separation and drying system of claim 2, wherein the infrared sensor in the irradiation zone performs real-time detection of biomass of maggots on the breeding tray within a scraping depth that a lower layer of scrapers in the intelligent scraping unit reach; when there are more than 20 maggots per square meter, the central control unit adjusts illuminating intensity and illuminating time of the intelligent light control unit and also adjusts a depth that the scrapers in the intelligent scraping unit reach.

8. The separation and drying system of claim 3, wherein the multi-layered scraper assembly is provided with the first weight sensor, so that a comparison is made between a weight of residues scraped by each layer of the scrapers and a weight of residues having a moisture content of 60% stored in the central control unit to start or stop scraping; when the scraped residues have a moisture content of more than 60%, a lower one of the layers of the scrapers stops scraping, and simultaneously the breeding tray is returned to a breeding area for standing.

\* \* \* \* \*